United States Patent [19]
Ogasawara et al.

[11] Patent Number: 5,900,369
[45] Date of Patent: May 4, 1999

[54] METHOD FOR PRODUCING OXODICYCLOPENTADIENE

[75] Inventors: Kunio Ogasawara; Takahiko Taniguchi, both of Sendai, Japan

[73] Assignee: Chisso Corporation, Osaka, Japan

[21] Appl. No.: 09/111,857

[22] Filed: Jul. 8, 1998

[30] Foreign Application Priority Data

Jul. 25, 1997 [JP] Japan ................................ 9-213840

[51] Int. Cl.$^6$ ............................ C12P 7/62; C07C 67/02
[52] U.S. Cl. ..................... 435/135; 560/256; 560/187; 560/239
[58] Field of Search ............................ 435/135; 560/256, 560/187, 239

[56] References Cited

U.S. PATENT DOCUMENTS

| | | | |
|---|---|---|---|
| 5,374,768 | 12/1994 | Takano et al. ................. | 560/256 |
| 5,442,098 | 8/1995 | Takano et al. ................. | 560/256 |
| 5,567,851 | 10/1996 | Takano et al. ................. | 568/354 |

FOREIGN PATENT DOCUMENTS

| | | |
|---|---|---|
| 0 428 302 | 5/1991 | European Pat. Off. . |
| 08113544 | 5/1996 | Japan . |

OTHER PUBLICATIONS

Takano, Seiichi et al., "Enantioconvergent route to alpha–cuparenone from dicyclopentadiene.", J. Chem. Soc. Chem. Commun., pp. 271–272 (1989).

Takano, Seiichi et al., "Expedient preparation and enantiomerization of optically pure dicyclopentadienone (tricyclo [5.1.0$^{2,6}$]deca–4,8–dien–3–one)." Synletters, pp. 636–638 (1991).

Tanaka, Keigo et al., "An expedient route to optically pure 3–endo–hydroxydicyclopentadiene.", Sythesis, pp. 1237–1239 (1995).

Taniguchi, Takahiko et al., "Lipase–triethylamine–mediated dynamic transesterification of a tricyclic acyloin having a latent meso–structure: a new route to optically pure oxydicyclopentadiene.", Chem. Commun., pp. 1399–1400 (1997).

Miller et al., Synthesis and Characterization . . . J. Org. Chem., vol. 41, No. 7, pp. 1221–1228, Apr. 1976.

Trost et al., Stereocontrolled Approach . . . J. Org. Chem., vol. 43, No. 24, pp. 4559–4564, Nov. 1978.

*Primary Examiner*—Samuel Barts
*Assistant Examiner*—Rosalynd Keys
*Attorney, Agent, or Firm*—Browdy and Neimark

[57] ABSTRACT

Optically active oxodicyclopentadiene is produced by adding lipase into ketoalcohol (1) and vinyl acetate, stirring them to obtain optically active acetate, and methylating and oxidizing to cleavage the reactant, and treating the product under basic conditions.

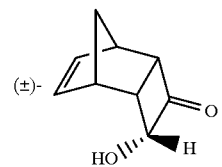

(1)

4 Claims, No Drawings

METHOD FOR PRODUCING OXODICYCLOPENTADIENE

BACKGROUND OF THE INVENTION

1. Field of the Invention

The present invention relates to a new method for producing optically active oxodicyclopentadiene which is an intermediate of pharmaceutical products and the like.

2. Description of the Prior Art

The optically active oxocyclopentadiene is very useful for starting materials of physiologically active materials such as pharmaceutical products. For example, it is known that the compound is a starting material of Aphanorphine having analgesic effect (J. Chem. Soc. Chem. Commun., 290 (1990)).

However, a well-known methods for producing the optically active oxocyclopentadiene uses optical resolution (J. Chem. Soc. Chem. Commun., 271 (1989), Synlett., 636 (1991), and Synthesis, 1237 (1995)), so that one of the enantiomers becomes useless. Accordingly, to use the one, it should be reacted via several steps to obtain the antipode.

SUMMARY OF THE INVENTION

The present inventors earnestly studied a method for producing only one of the enantiomers of optically active oxodicyclopentadiene, and the present invention has been completed by finding a method for producing optically active oxodicyclopentadiene represented by formula (4):

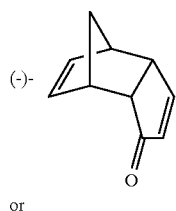

(4)

or

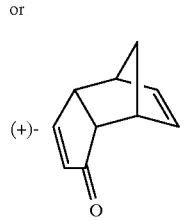

comprising reacting an acyloin compound as a starting material represented by formula (1):

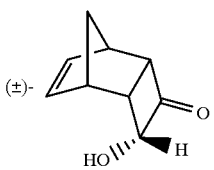

(1)

with an acylating agent in the presence of lipase, and obtaining either (+)-or (−) of the esters represented by formula (2):

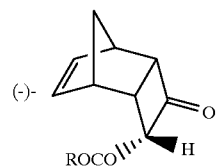

(2)

or

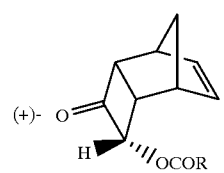

wherein R indicates straight or branched alkyl, alkoxy, alkenyl or alkenyloxy, further, introducing a methyl group to obtain a new optically active diol represented by formula (3):

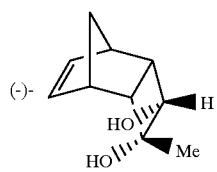

(3)

or

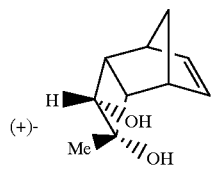

using the diol as an intermediate, and obtaining optically active oxodicyclopentadiene represented by the above formula (4).

The present invention is represented by the following reaction formula. For convenience sake, the case for obtaining a (−) material is shown:

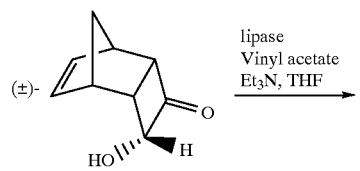

(1)

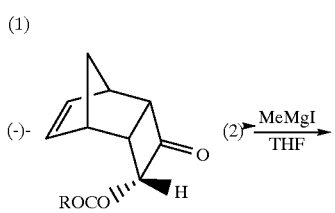

(2)

-continued

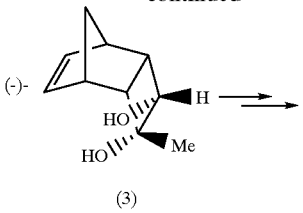
(3)

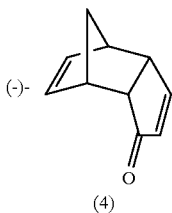
(4)

Compound (1) of the starting material can be introduced via bistrimethylsiloxy compound (7) from endo-2,3-dicarbomethoxybicyclo[2,2, 1] hepta-5-ene (6) which is easily available by a method of Miller et al (J. Org. Chem., 41, 1221 (1976)).

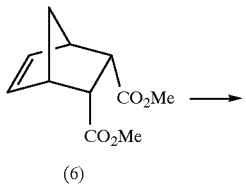
(6)

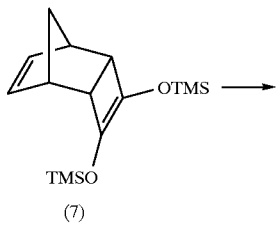
(7)

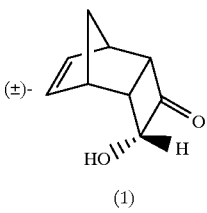
(1)

The resulting compound (1) is then reacted with an acylating agent in the presence of lipase. Commercially available lipase may be used. As embodiments of the lipase, Lipase PS (manufactured by Amano Pharmaceutical Co., Ltd.), Toyoteam LIP (manufactured by Toyobo Co., Ltd.), Novozyme 435 (manufactured by Novo Nordisk) and the like can be exemplified.

Moreover, it is possible to use dry microorganisms and protein as it is extracted and refined from a culture solution. As the kind of lipase, particularly, the material derived from Pseudomonas is preferably used.

As acylating agents, fatty esters, acid anhydrides, triglycerides, trichloroethyl ester, vinyl esters can be exemplified. Particularly preferred agents are vinyl esters, such as vinyl acetate, vinyl propionate, vinyl capronate and vinyl stearate. Further, isopropenyl acetate also can be used.

As reaction solvents, hexane, heptane, cyclohexane, benzene, toluene, 1,2-dichloroethane, dioxane, diethyl ether, diisopropyl ether, dibutyl ether, t-butylmethyl ether, THF, acetone, acetonitrile and DMSO can be exemplified. As additives, triethylamine can be added, and the rate is 1–30%, and preferably 10%.

The reaction temperature is suitably 10–100° C., and preferably 20–45° C. The reaction time is 1–1000 hours, and preferably 30–50 hours.

Such obtained compounds (2) are methylated with methyl magnesium iodide or dimethyl copper lithium which is a common methylating agent to obtain methylated compound (3).

Compound (3) is cleavaged in the presence of periodic acid to obtain ketoaldehyde represented by formula (5).

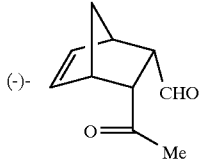

or

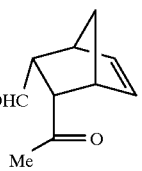

(5)

After the resulting aldehyde (5) is exposed to, for example, an aqueous alcohol solution containing sodium hydroxide and the like and treated under basic conditions, it is able to obtain compound (4).

By using the production method of the present invention, useful intermediates represented by formula (3) can be prepared, and from the compound (3), optically active oxodicyclopentadiene useful as a starting material for synthesizing many physiologically active materials can be obtained.

DESCRIPTION OF THE PREFERRED EMBODIMENTS

The following Examples are intended to further illustrate the present invention and not to limit the invention by these Examples.

EXAMPLE 1

Synthesis of (−)-ketoacetate (2)

To a THF solution (80 ml) of ketoalcohol (1) (4.5 g, 30 mmol), Et$_3$N (0.4 ml, 3 mmol) and vinyl acetate (3.3 ml, 36 mmol), and then Lipase PS (4.5 g, manufactured by Amano Pharmaceutical Co., Ltd.) were added, and the mixture was stirred at room temperature for 48 hours. After completing the reaction, the reaction solution was filtered with Celite, and the solvent was distilled off under reduced pressure. To the residue water was added and the mixture was extracted with Et$_2$O, the organic layer was washed with a saturated aqueous solution of NaCl and dried with MgSO$_4$, and the solvent was distilled off under reduced pressure.

The residue was purified by silica gel chromatography (eluent: Et$_2$O/hexane=1/3 v/v), and colorless solid (−)-ketoacetate (2) (4.3 g, 75%) was obtained. Then, ketoalcohol (0.4 g) of the starting material was recovered.

$[\alpha]_D^{24}$ −120.7° (c2.0, CHCl$_3$), mp 28° C. (Et$_2$O/hexane); IR (nujor, cm$^{-1}$) 1786, 1743; $^1$H-NMR (300 MHz, CDCl$_3$) d 6.14 (dd, J=5.5, 3.0 Hz, 1H), 6.01 (dd, J=5.5, 2.7 Hz, 1H), 5.35 (dd, J=8.8, 3.3 Hz, 1H), 3.63 (ddd, J=7.4, 5.5, 3.3 Hz, 1H), 3.39 (ddd, J=8.8, 5.5, 4.7 Hz, 1H), 3.23–3.17 (m, 1H), 3.15–3.09 (m, 1H), 2.08 (s, 3H), 1.77 (br d, J=8.5 Hz, 1H), 1.53 (br d, J=8.5 Hz, 1H); HRMS m/z $C_{11}H_{12}O_3$ ($M^+$) calcd 192.0786, obsd 192.0828.

To an anhydrous THF solution (13 ml) of ketoacetate (2) (0.6 g, 3.1 mmol), a MeMgI solution (15.5 ml, 1.0M in THF) solution was added at a temperature of −78° C., and the mixture was stirred at the same temperature for 2 hours. After completing the reaction, the reactant was diluted with $Et_2O$, added $H_2O$ under ice cooling, and stirred for 5 minutes. The organic layer was washed with a saturated aqueous solution of NaCl, dried over $MgSO_4$, and the solvent was distilled away under reduced pressure.

The residue was purified by silica gel chromatography (eluent: AcOEt/hexane=1/5 v/v), and colorless solid (−)-diol (3) (0.43 g, 83%) was obtained (eluent: AcOEt/hexane=1/5 v/v).

$[\alpha]_D^{26}$ −15.7° (c0.6, $CHCl_3$), mp 107° C. (AcOEt/hexane); IR (nujor, $cm^{-1}$) 3394; $^1$H NMR (300 MHz, $CDCl_3$) d 6.39–6.34 (br s, 2H), 3.87 (br d, J=7.1 Hz, 1H), 3.03–3.00 (m, 2H), 2.86–2.80 (m, 1H), 2.62 (ddd, J=6.9, 4.9, 1.9 Hz, 1H), 2.20 (br s, 1H), 1.99 (br s, 1H), 1.47 (d, J=8.0 Hz, 1H), 1.32 (s, 3H), 1.11 (d, J=8.0 Hz, 1H); HRMS m/z $C_{10}H_{14}O_2$($M^+$) calcd 166.0993, obsd 166.1019.

To a THF-$H_2O$ mixture solution (2:1 v/v, 3 ml) of (−)-diol (3) (80 mg, 0.5 mmol), $NaIO_4$ (0.5 g, 2.5 mmol) was added under ice cooling, and the mixture was stirred for 2 hours. After completing the reaction, the reactant was diluted with $Et_2O$, the organic layer was washed with $H_2O$ and a saturated aqueous solution of NaCl, and dried over $MgSO_4$, and the solvent was distilled away under reduced pressure to obtain crude ketoaldehyde (5). The product was used for next reaction without purification.

To an EtOH solution (3 ml) of the above-mentioned crude ketoaldehyde (5), an aqueous solution of 2% NaOH (1 ml) was added, and the mixture was stirred for 12 hours. After completing the reaction, an aqueous solution of 1% HCl was added under ice cooling to neutralized the reactant, and the solvent was distilled away under reduced pressure. Water was added to the residue, the mixture was extracted with $Et_2O$, the organic layer was washed with a saturated aqueous solution of NaCl and dried with $MgSO_4$, and the solvent was distilled away under reduced pressure. The residue was purified by silica gel chromatography (eluent: $Et_2O$/hexane= 1/3 v/v), and colorless solid (−)-oxodicyclopentadiene (4) (38 mg, 54% for 2 steps) was obtained. The spectral data were agreed with values of references.

$[\alpha]_D^{26}$ −154° (c 1.0, $CHCl_3$), mp 74° C. (hexane); referenced value $[\alpha]_D^{29}$ −158.5° (c 1.0, $CHCl_3$), mp 76° C.

We claim:

1. A new method for producing an optically active ester represented by the following general formula (2):

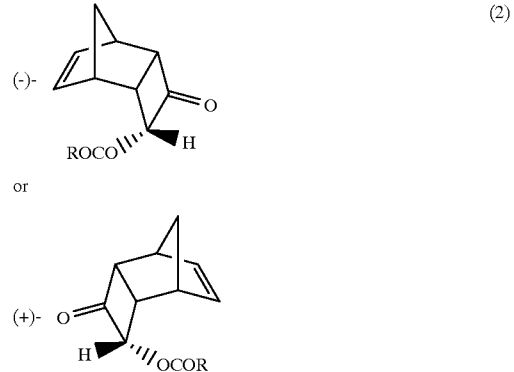

wherein R indicates straight or branched alkyl, alkoxy, alkenyl or alkenyloxy, comprising reacting an acyloin compound as a starting material represented by the following formula:

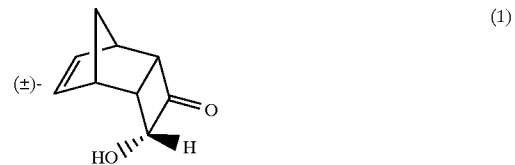

with an acylating agent in the presence of lipase, and obtaining either (+)-or (−) of the esters represented by the above formula (2).

2. A method for producing an optically active ester claimed in claim 1, wherein the lipase is derived from Pseudomonas.

3. A method for producing an optically active ester claimed in claim 1, wherein the acylating agent is a vinyl ester.

4. A method for producing an optically active ester claimed in claim 1, wherein the lipase is derived from Pseudomonas and the acylating agent is a vinyl ester.

* * * * *